(12) United States Patent
Laugere et al.

(10) Patent No.: US 10,065,002 B2
(45) Date of Patent: Sep. 4, 2018

(54) DISPENSE INTERFACE

(71) Applicant: SANOFI-AVENTIS DEUTSCHLAND GMBH, Frankfurt am Main (DE)

(72) Inventors: Frederic Laugere, Bedfordshire (GB); Cristian Popa, Norfolk (GB); Ben Impey, Cambridgeshire (GB); Andrew Macleod, Cambridgeshire (GB)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 501 days.

(21) Appl. No.: 14/395,995

(22) PCT Filed: May 16, 2013

(86) PCT No.: PCT/EP2013/060168
§ 371 (c)(1),
(2) Date: Oct. 21, 2014

(87) PCT Pub. No.: WO2013/171315
PCT Pub. Date: Nov. 21, 2013

(65) Prior Publication Data
US 2015/0112253 A1   Apr. 23, 2015

(30) Foreign Application Priority Data
May 16, 2012   (EP) .................................... 12168378

(51) Int. Cl.
*A61M 37/00*   (2006.01)
*A61M 5/315*   (2006.01)
(Continued)

(52) U.S. Cl.
CPC .......... *A61M 5/31596* (2013.01); *A61M 5/19* (2013.01); *A61M 5/20* (2013.01);
(Continued)

(58) Field of Classification Search
CPC .............. A61M 5/162; A61M 5/16827; A61M 2005/3128
(Continued)

(56) References Cited

U.S. PATENT DOCUMENTS 5,329,976 A * 7/1994 Haber .................. A61J 1/2089
141/18
5,478,323 A   12/1995 Westwood et al.
(Continued)

FOREIGN PATENT DOCUMENTS

CN   201759943 U   3/2011
WO   92/15345   9/1992
(Continued)

OTHER PUBLICATIONS

Chinese Search Report for CN Application No. 201380023729.4, dated May 26, 2016.
(Continued)

*Primary Examiner* — Phillip Gray
(74) *Attorney, Agent, or Firm* — McCarter & English, LLP

(57) ABSTRACT

The present application relates to a dispense interface comprising at least a first flat part tightly connected with a second flat part, wherein at least one of the at least two flat parts comprises at least one deepening configured for forming at least one part of a channel profile, wherein the at least one deepening is formed by embossing, wherein the channel profile comprises at least a first inlet channel and a second inlet channel and at least one outlet channel, wherein each of the at least two inlet channels is configured for fluid communication with a respective reservoir of at least two reservoirs.

15 Claims, 14 Drawing Sheets

(51) Int. Cl.
  *A61M 5/19*     (2006.01)
  *A61M 5/20*     (2006.01)
  *A61M 5/24*       (2006.01)
  *A61M 5/31*       (2006.01)

(52) U.S. Cl.
  CPC . *A61M 5/31546* (2013.01); *A61M 2005/2407* (2013.01); *A61M 2005/2496* (2013.01); *A61M 2005/3128* (2013.01); *A61M 2005/31588* (2013.01); *A61M 2207/00* (2013.01); *Y10T 29/49826* (2015.01)

(58) Field of Classification Search
  USPC .................................................. 604/87, 191
  See application file for complete search history.

(56)     References Cited

U.S. PATENT DOCUMENTS

2003/0120217  A1     6/2003  Abergel
  2010/0288380  A1*   11/2010  Sicre ................... F28D 9/0037
                                                     137/561 R

FOREIGN PATENT DOCUMENTS

WO         94/11039       5/1994
  WO       2010/139668 A1  12/2010

OTHER PUBLICATIONS

International Search Report for Int. App. No. PCT/EP2013/060168, dated Oct. 4, 2013.

* cited by examiner

DISPENSE INTERFACE

CROSS REFERENCE TO RELATED APPLICATIONS

The present application is a U.S. National Phase application pursuant to 35 U.S.C. § 371 of International Application No. PCT/EP2013/060168 filed May 16, 2013, which claims priority to European Patent Application No. 12168378.3 filed May 16, 2012. The entire disclosure contents of these applications are herewith incorporated by reference into the present application.

TECHNICAL FIELD

The present patent application relates to an ejection device, for example a medical device, for delivering at least two liquids, such as liquid drug agents, from separate reservoirs. Such drug agents may comprise a first and a second medicament. The medical device includes a dose setting mechanism for delivering the drug agents automatically or manually by the user.

SUMMARY

The medical device can be an injector, for example a hand-held injector, especially a pen-type injector, that is an injector of the kind that provides for administration by injection of medicinal products from one or more multidose cartridges. In particular, the present invention relates to such injectors where a user may set the dose.

The drug agents may be contained in two or more multiple dose reservoirs, containers or packages, each containing independent (single drug compound) or pre-mixed (co-formulated multiple drug compounds) drug agents.

Certain disease states require treatment using one or more different medicaments. Some drug compounds need to be delivered in a specific relationship with each other in order to deliver the optimum therapeutic dose. The present patent application is of particular benefit where combination therapy is desirable, but not possible in a single formulation for reasons such as, but not limited to, stability, compromised therapeutic performance and toxicology.

For example, in some cases it may be beneficial to treat a diabetic with a long acting insulin (also may be referred to as the first or primary medicament) along with a glucagon-like peptide-1 such as GLP-1 or GLP-1 analog (also may be referred to as the second drug or secondary medicament).

Accordingly, there exists a need to provide devices for the delivery of two or more medicaments in a single injection or delivery step that is simple for the user to perform without complicated physical manipulations of the drug delivery device. The proposed drug delivery device provides separate storage containers or cartridge retainers for two or more active drug agents. These active drug agents are then combined and/or delivered to the patient during a single delivery procedure. These active agents may be administered together in a combined dose or alternatively, these active agents may be combined in a sequential manner, one after the other.

The drug delivery device also allows for the opportunity of varying the quantity of the medicaments. For example, one fluid quantity can be varied by changing the properties of the injection device (e.g., setting a user variable dose or changing the device's "fixed" dose). The second medicament quantity can be changed by manufacturing a variety of secondary drug containing packages with each variant containing a different volume and/or concentration of the second active agent.

The drug delivery device may have a single dispense interface. This interface may be configured for fluid communication with a primary reservoir and with a secondary reservoir of medicament containing at least one drug agent. The drug dispense interface can be a type of outlet that allows the two or more medicaments to exit the system and be delivered to the patient.

The combination of compounds from separate reservoirs can be delivered to the body via a double-ended needle assembly. This provides a combination drug injection system that, from a user's perspective, achieves drug delivery in a manner that closely matches the currently available injection devices that use standard needle assemblies. One possible delivery procedure may involve the following steps:

1. Attach a dispense interface to a distal end of the electro-mechanical injection device. The dispense interface comprises a first and a second proximal needle. The first and second needles pierce a first reservoir containing a primary compound and a second reservoir containing a secondary compound, respectively.

2. Attach a dose dispenser, such as a double-ended needle assembly, to a distal end of the dispense interface. In this manner, a proximal end of the needle assembly is in fluidic communication with both the primary compound and secondary compound.

3. Dial up/set a desired dose of the primary compound from the injection device, for example, via a graphical user interface (GUI).

4. After the user sets the dose of the primary compound, the micro-processor controlled control unit may determine or compute a dose of the secondary compound and preferably may determine or compute this second dose based on a previously stored therapeutic dose profile. It is this computed combination of medicaments that will then be injected by the user. The therapeutic dose profile may be user selectable. Alternatively, the user can dial or set a desired dose of the secondary compound.

5. Optionally, after the second dose has been set, the device may be placed in an armed condition. The optional armed condition may be achieved by pressing and/or holding an "OK" or an "Arm" button on a control panel. The armed condition may be provided for a predefined period of time during which the device can be used to dispense the combined dose.

6. Then, the user will insert or apply the distal end of the dose dispenser (e.g. a double ended needle assembly) into the desired injection site. The dose of the combination of the primary compound and the secondary compound (and potentially a third medicament) is administered by activating an injection user interface (e.g. an injection button).

Both medicaments may be delivered via one injection needle or dose dispenser and in one injection step. This offers a convenient benefit to the user in terms of reduced user steps compared to administering two separate injections.

The dispense interfaces in the state of the art are, however, often of complex design. In order to provide the manifold to lead the medicaments from two different reservoirs to a single outlet, multiple complex and/or small parts need to be produced and assembled. In particular, small parts having a complex shape must be molded with a high accuracy. Besides the need of complex and special cavities for forming the respective parts, the assembly of the molded parts and the integration of the needles can be complex as well. The complex part structures and the corresponding complicated assembly steps may cause the dispense interface to be difficult to manufacture and expensive.

Additionally, the dispense interface is regularly kept at the drug delivery device for a longer period of time. This means that only the dose dispenser in form of a double ended needle, for instance, is exchanged for every or nearly every injection procedure. The dispense interface, however, remains at the drug delivery device. An exchange of the dispense interface itself is regularly only necessary, when the reservoirs of the drug delivery device need to be exchanged.

This causes requirements for the material and design of the dispense interface to be fulfilled. Since the drug agents from the first and/or the second reservoir remain inside the dispense interface after a dispense procedure, a material compatibility of the parts of the dispense interface being in contact with the drug agents needs be to provided. No harmful substances must diffuse into the drug agents, since these would then be delivered to the patient with the next delivery procedure. Hence a biocompatibility is required, which guarantees that either no or negligible amounts of substances can diffuse into drug agents or are set free into the liquid.

Furthermore, if the dispense interface remains attached to the drug delivery device the different drug agents also start to diffuse into each other over time. A cross-contamination of the drug agents from one reservoir into the other reservoir needs to be prevented for the above mentioned reasons of stability, compromised therapeutic performance and toxicology, for example.

In order to prevent such cross-contaminations, non-return valves can be implemented in the dispense interface. This, however, increases the part count and thus the complexity and cost during the production of the dispense interface. Additionally, a septum is often provided at the outlet of the dispense interface, since the dispense interface needs to be sealed, when it is connected to the reservoirs but there is no dose dispenser attached.

In light of the aforementioned, the invention faces the technical problem of reducing the complexity and providing an easy manufacture and usage of the dispense interface and at the same time overcoming the problems of material compatibility and cross contamination.

The technical problem is solved by a dispense interface comprising at least a first flat part tightly connected with a second flat part, wherein at least one of the at least two flat parts comprises at least one deepening configured for forming at least one part of a channel profile, wherein the at least one deepening is formed by embossing, wherein the channel profile comprises at least a first inlet channel and a second inlet channel and at least one outlet channel and wherein each of the at least two inlet channels is configured for fluid communication with a respective reservoir of at least two reservoirs.

By providing a dispense interface having a first flat part which is tightly joined with a second flat part, wherein at least one of these flat parts comprises a deepening configured for forming at least one part of the channel structure, the production and assembly of the dispense interface can be kept simple. Particularly advantageous is that the at least one deepening, preferably all deepenings, are formed by embossing, in particular, cold-embossing. Embossing is a process for producing raised or sunken designs or relief in flat parts, such as metallic flat parts. A desired channel structure comprising at least two inlet channels connected to an outlet channel can be formed easily.

The cost efficient and easy production process allows the dispense interface to be replaced frequently, thus reducing the risk of contamination. In particular, it enables the dispense interface to be used as a single-use item. This means that after a single delivery procedure with an ejection of a liquid or a drug agent through the dispense interface the dispense interface can be detached from the ejection device and discarded.

The ejection device can, for instance, be a medical device such as a drug delivery device.

During an ejection procedure a liquid may enter the dispense interface through the first inlet channel and another liquid may enter the dispense interface through the second inlet channel which are a part of the channel profile. The liquids can leave the dispense interface via the outlet channel which is also a part of the channel profile. The dispense interface can be seen as a manifold.

Since the dispense interface is only in connection with the reservoirs of the ejection device substantially during the ejection procedure, there is only a short time for possible substances or chemicals in the dispense interface to diffuse into the liquid ejected by the ejection device and guided through the inlet and outlet channels.

There is also substantially no time for the liquids within the reservoirs to become cross-contaminated, since the dispense interface is directly detached after the ejection procedure as it can be thrown away.

Furthermore there is no need for a septum in the dispense interface, since an exchange of the third needle assembly is not necessary, since after each injection an exchange of the whole dispense interface can take place.

As a consequence of the above mentioned, the complexity of the dispense interface is reduced, an easy usage and manufacturing of the dispense interface is provided and at the same time the problems of material compatibility and cross-contamination are overcome.

According to an embodiment of the dispense interface of the invention, at least one of the at least two flat parts comprises a first deepening configured for forming at least one part of the first inlet channel, at least one of the at least two flat parts comprises a second deepening configured for forming at least one part of the second inlet channel and wherein at least one of the at least two flat parts comprises a third deepening configured for forming at least one part of the outlet channel. In particular, all channels or hollow chambers can be formed by deepenings. A desired relief can be introduced in at least one flat part. By joining the flat parts comprising the at least three deepenings, the desired channel structure can be established. The production of a dispense interface can be kept particularly simple since deepenings can be formed easily by embossing, in particular, cold embossing. For instance, embossing can be performed by means of matched male and female roller dies, or by passing a flat part between rolls of the desired pattern.

It is preferred, if at least the embossed flat part is a metallic plate. Embossing is particular suitable for forming raised or sunken designs or reliefs in metallic flat parts. For instance, the metallic plate is made of aluminium. It shall be understood that according to other variants of the invention, other metals can be used.

Deepenings can be formed by embossing particularly easily if the metallic plate is a metallic foil comprising a thickness of at most 0.2 mm. A desired relief can easily be introduced due to the thin design of the flat part.

It has been found that for forming a channel structure, all deepenings can be formed only in one flat part, while the other flat part can be free of any deepening. Only one flat part has to be processed. Thus, the production cost can be reduced. As a further consequence, a low-cost material can be used for the second flat part. In particular, it is not required to use a metallic material. According to a preferred embodiment of the dispense interface of the invention, at least one of the at least two flat parts is made of a polymer material. A polymer flat part can be processed and formed easily. Furthermore, a polymer flat part can be joined to the other flat part, like a metallic flat part, in an easy way.

Alternatively, according to another embodiment, at least one part of the channel profile is formed by embossing at least the first flat part and the second flat part. For instance, both flat parts can be metallic flat parts. In particular, the metallic flat parts can be made of the same material. By forming deepenings in both the first flat part and the second flat part, more complex channel structures can be formed.

According to a preferred embodiment, at least one deepening configured for forming at least one part of a first half channel profile is formed in the first flat part and at least one deepening configured for forming at least one part of a second half channel profile corresponding to the first half channel profile is formed in the second flat part. At least one deepening of the first flat part may correspond to at least one deepening of the second flat part. In particular, the first flat part may comprise a first half channel profile corresponding to a second half channel profile which is integrated in the second flat part. By joining the two flat parts to each other, a channel structure can be established.

The tight connection, in particular, a fluid tight connection, between the at least two flat parts can be made arbitrarily and may especially depend on the materials of the at least two flat parts. It is preferred if the tight connection between the at least two flat parts is formed by ultrasonic welding techniques, heat sealing techniques, adhesive bonding techniques and/or spot welding techniques.

In a further embodiment of the dispense interface according to the invention, each of the at least two inlet channels comprises an inlet opening, wherein the at least one outlet opening comprises an outlet opening and wherein at least one of the inlet or outlet openings is provided with a needle. Preferably, a first and second proximal needle and an ejection needle can be integrated in the dispense interface. For instance, before joining the at least two flat parts to each other, the respective needles can be inserted. The flat parts can then be tightly connected together with the needles resulting in a compact dispense interface comprising at least one, preferably the first and second proximal needle and the ejection needle. Further needle assemblies to be attached for using an ejection device are not needed. A simple and user friendly handling can be provided.

It is preferred if the at least one needle is tightly integrated in one of the inlet and outlet openings by press fitting and/or potting. By using these techniques, the production and assembling of the interface can be kept simple. It may be possible to join the at least two flat parts to each other in a first step. Afterwards, the needles can be tightly integrated by e.g. press fitting and/or potting.

It shall be understood that alternatively, separate needle assemblies connectable to the dispense interface can be provided.

When the inlet and outlet channels are configured such that a liquid can flow freely from any region of higher pressure to any region of lower pressure, the dispense interface is particularly easy and cost efficient to manufacture. No components, in particular valves, are provided in the respective channels, which would increase the efforts and cost during the manufacture of the dispense interface. The risk of a cross-contamination or a diffusion of substances into the liquid guided with the dispense interface is counteracted by the fact that the dispense interface can be produced so efficiently and cost-effectively, that the dispense interface can be used as a single-use item. Hence, there is only a short period of time, in which the guided liquid and the dispense interface are in contact reducing the risk of any contaminations of the dispense interface.

Alternatively, it is also possible that the channel profile comprises at least one non-return valve. In particular, a connecting channel configured for fluid communication between the first and second inlet channel and the outlet channel can be provided. The connecting channel may comprise such a valve. This prevents or minimizes the back flow of a fluid back into one of the reservoirs. Additionally, the common volume can be reduced, in which both fluids from the reservoirs mix. This is advantageous, in case the user forgets to remove the dispense interface from the ejection device. In that case a cross-contamination can still be prevented. Especially, when the fluids are ejected one after another, the risk of a cross-contamination is higher, since there is a reduced counter pressure for the fluid from the one reservoir to enter the other reservoir compared to when both fluids are ejected simultaneously. Preferably, either a valve, such as a diaphragm valve, for each the first and the second inlet channels is provided or a valve, such as a shuttle valve, which prevents backflow in both the first and the second inlet channels is provided. In case more than two inlet channels are provided, a corresponding number of valves is preferably provided.

The at least one valve can either be an integral part of the dispense interface or the at least one valve can also be designed as a separate part and then assembled with the first flat part and/or the second flat part. Possible valves are for example a diaphragm or flap valve, a shuttle valve, a molded duck bill valve, a flat spring, or rotation flap valve.

The technical problem is further solved by a method for manufacturing a dispense interface comprising the steps of providing at least a first flat part and a second flat part, forming at least one deepening into at least one of the at least two flat parts by embossing, and tightly connecting the first flat part to the second flat part.

By manufacturing a dispense interface having a first flat part and a second flat part, wherein at least one deepening is formed into one of these parts by embossing, in particular cold-embossing, the production and assembly of the dispense interface can be kept simple and cheap. Embossing is advantageous since it is a simple process for producing raised or sunken designs or relief in flat parts, such as metallic flat parts.

As a consequence of the above mentioned, the dispense interface can be manufactured easily with low cost.

The technical problem is further solved by a system comprising a previously described dispense interface and an ejection device, wherein the dispense interface is attached to the ejection interface.

The user can attach the dispense interface directly before an ejection procedure. For this purpose, connection elements may be provided. Preferably, the needles are already integrated in the dispense interface. Further steps, like attaching a first needle assembly and attaching a second needle assembly can be omitted. The dispense interface can be exchanged more frequently, or even after every use.

As a consequence, the complexity of the dispense interface can be reduced, an easy usage of the dispense interface can be provided and at the same time the problems of material compatibility and cross contamination are overcome.

According to an embodiment of the system according to the invention, the ejection device is a medical device for delivering at least two drug agents from at least two separate reservoirs.

The technical problem is further solved by a method for using the previously described system comprising attaching the dispense interface to an ejection device having at least two reservoirs such that a fluid tight connection is established between said at least two reservoirs and the dispense interface, ejecting a fluid from at least one of the reservoirs out of the dispense interface, and detaching the dispense interface from the ejection device.

Preferably, the needles are integrated in the dispense interface. Further steps for attaching a separate needle assembly can be omitted. Preferably, the user attaches the dispense interface to the ejection device after taking the dispense interface out of a package. It is in particular possible and still economical for the user, to exchange the dispense interface more frequently, or even after every use.

Since the needle assemblies can be integrated in the dispense interface, an easy usage of the dispense interface is provided. At the same time the problems of material compatibility and cross contamination are overcome, since the user establishes the connection of the dispense interface with the reservoirs directly before an ejection and the user can remove it directly afterwards as well.

When the user attaches the dispense interface to the ejection device, preferably the first proximal needle provides a fluid tight connection to the first reservoir of the ejection device, for example by piercing a septum of the first reservoir, while the second proximal needle provides a fluid tight connection to the second reservoir of the ejection device, for example by piercing a septum of the second reservoir.

The dispense interface may be secured in an engaged position with the ejection device. This can be done by fixing elements provided by the ejection device, for example. Such fixing elements, hooks or protrusions adapted to the dispense interface for instance, may establish a positive fit between the dispense interface and the ejection device. Alternatively, it is also possible that the dispense interface is fixed in the engaged position with the ejection device only by friction fit.

In case the needle tips of the first and second needle assemblies are covered with safety elements, e.g. needle covers, the user needs to remove these covers before attaching the dispense interface to the ejection device. In case the needle tip of the third needle is covered with a safety element, like a needle cover, the user needs to remove this cover before performing an ejection procedure.

Preferably, the method according to the invention further comprises the steps of ejecting a fluid from at least one of the reservoirs through the dispense interface and then removing the dispense interface from the ejection device.

These steps are performed after having attached the dispense interface to the injection device. When the dispense interface is removed after an ejection procedure, for example by the user, the risk of possible contaminations of the fluids and/or the reservoirs is reduced. Preferably, the dispense interface is removed directly after an ejection procedure. The dispense interface can then be discarded with the (integrated) needles.

These as well as other advantages of various aspects of the present invention will become apparent to those of ordinary skill in the art by reading the following detailed description, with appropriate reference to the accompanying drawings, in which:

DETAILED DESCRIPTION

Figure 1:
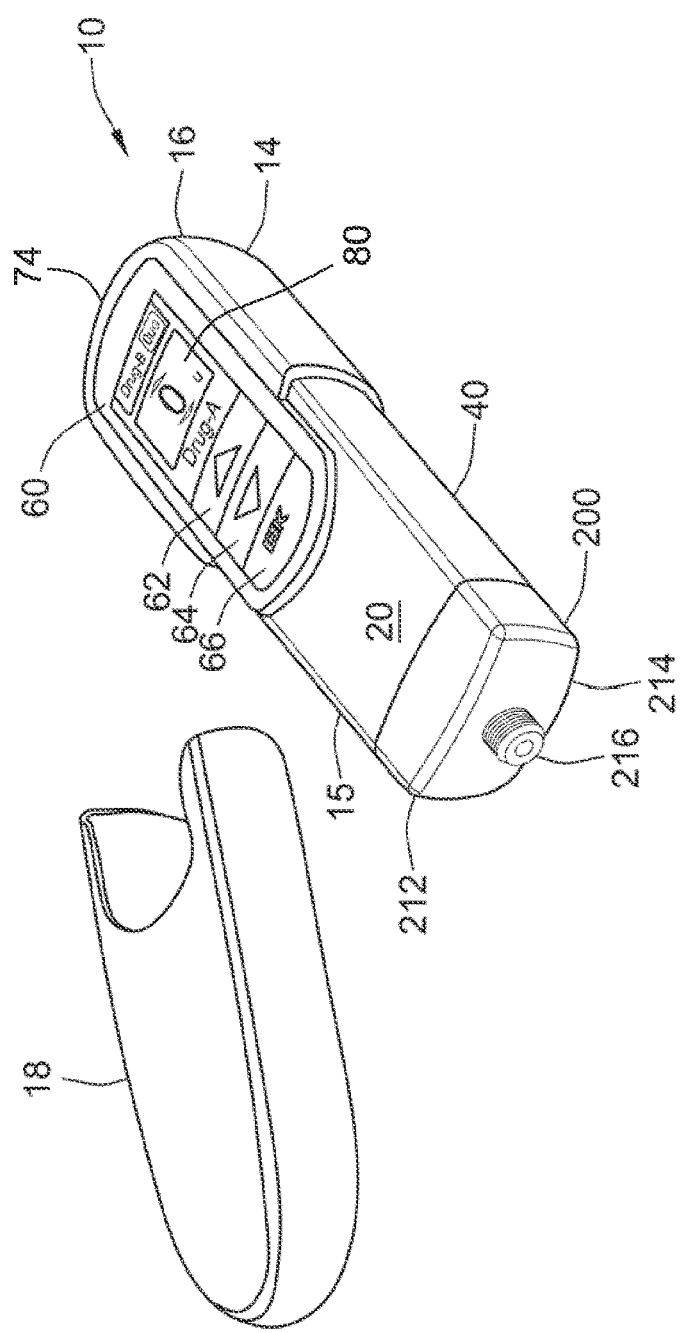
FIG. 1 illustrates a perspective view of a delivery device with an end cap of the device removed.
Figure 2:
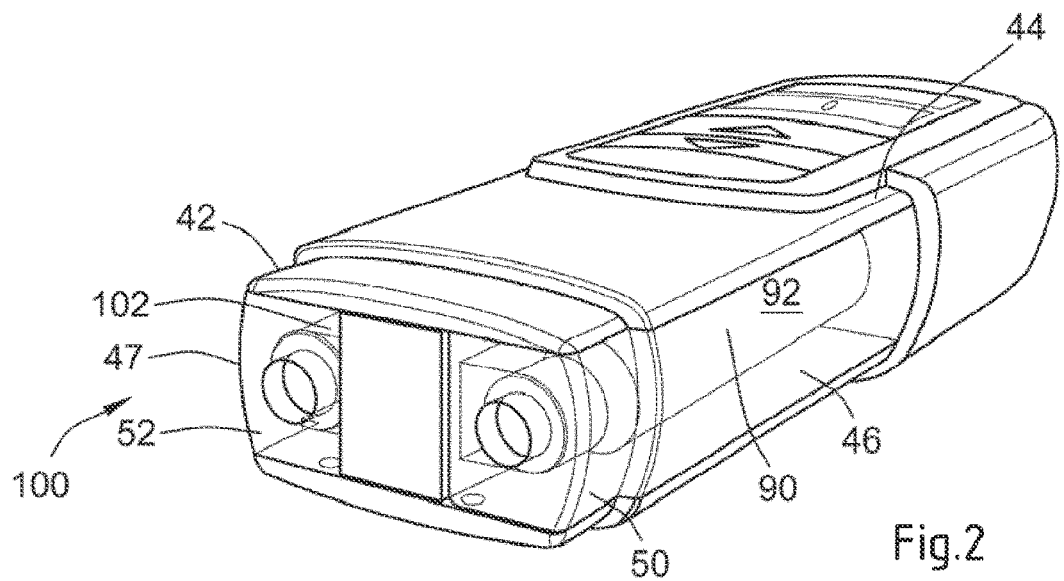
FIG. 2 illustrates a perspective view of the delivery device distal end showing the cartridge.

A ejection device in form of a drug delivery device illustrated in FIG. 1 comprises a main body 14 that extends from a proximal end 16 to a distal end 15. At the distal end 15, a removable end cap or cover 18 is provided. This end cap 18 and the distal end 15 of the main body 14 work together to provide a snap fit or form fit connection so that once the cover 18 is slid onto the distal end 15 of the main body 14, this frictional fit between the cap and the main body outer surface 20 prevents the cover from inadvertently falling off the main body.

The main body 14 contains a micro-processor control unit, an electro-mechanical drive train, and at least two medicament reservoirs. When the end cap or cover 18 is removed from the device 10 (as illustrated in FIG. 1), a dispense interface 200 is mounted to the distal end 15 of the main body 14, and a dose dispenser (e.g., a needle assembly) is attached to the interface. The drug delivery device 10 can be used to administer a computed dose of a second medicament (secondary drug compound) and a variable dose of a first medicament (primary drug compound) through a single needle assembly, such as a double ended needle assembly.

The drive train may exert a pressure on the bung of each cartridge, respectively, in order to expel the doses of the first and second medicaments. For example, a piston rod may push the bung of a cartridge forward a pre-determined amount for a single dose of medicament. When the cartridge is empty, the piston rod is retracted completely inside the main body 14, so that the empty cartridge can be removed and a new cartridge can be inserted.

A control panel region 60 is provided near the proximal end of the main body 14. Preferably, this control panel region 60 comprises a digital display 80 along with a plurality of human interface elements that can be manipulated by a user to set and inject a combined dose. In this arrangement, the control panel region comprises a first dose setting button 62, a second dose setting button 64 and a third button 66 designated with the symbol "OK." In addition, along the most proximal end of the main body, an injection button 74 is also provided (not visible in the perspective view of FIG. 1). The user interface of the drug delivery device may comprise additional buttons, such as a "menu" button, a "back" button, or a "light" button to switch on an illumination of the display.

The cartridge holder 40 can be removably attached to the main body 14 and may contain at least two cartridge retainers 50 and 52. Each retainer is configured so as to contain one medicament reservoir, such as a glass cartridge. Preferably, each cartridge contains a different medicament.

In addition, at the distal end of the cartridge holder 40, the drug delivery device illustrated in FIG. 1 includes a dispense interface 200. As will be described in relation to FIG. 4, in one arrangement, this dispense interface 200 includes a main outer body 210 that is removably attached to a distal end 42 of the cartridge housing 40. As can be seen in FIG. 1, a distal end 214 of the dispense interface 200 preferably comprises a needle hub 216. This needle hub 216 may be configured so as to allow a dose dispenser, such as a conventional pen type injection needle assembly, to be removably mounted to the drug delivery device 10.

Once the device is turned on, the digital display 80 shown in FIG. 1 illuminates and provides the user certain device information, preferably information relating to the medicaments contained within the cartridge holder 40. For example, the user is provided with certain information relating to both the primary medicament (Drug A) and the secondary medicament (Drug B).

Figure 3:
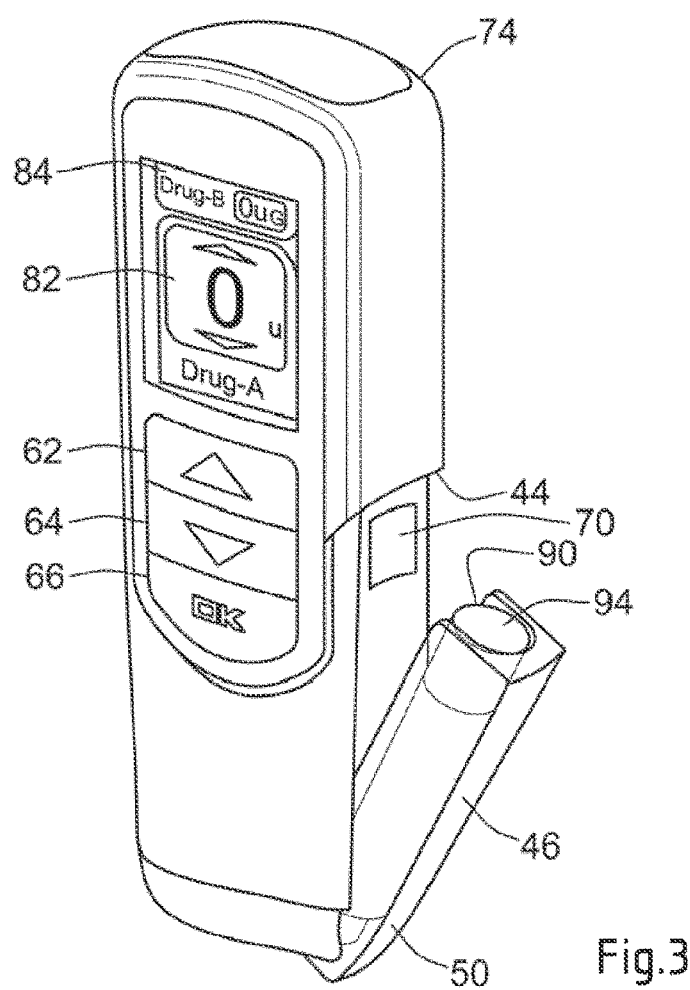
FIG. 3 illustrates a perspective view of the delivery device illustrated in FIG. 1 or 2 with one cartridge retainer in an open position.

As shown in FIG. 3, the first and second cartridge retainers 50, 52 may be hinged cartridge retainers. These hinged retainers allow user access to the cartridges. FIG. 3 illustrates a perspective view of the cartridge holder 40 illustrated in FIG. 1 with the first hinged cartridge retainer 50 in an open position. FIG. 3 illustrates how a user might access the first cartridge 90 by opening up the first retainer 50 and thereby having access to the first cartridge 90.

Figure 4:
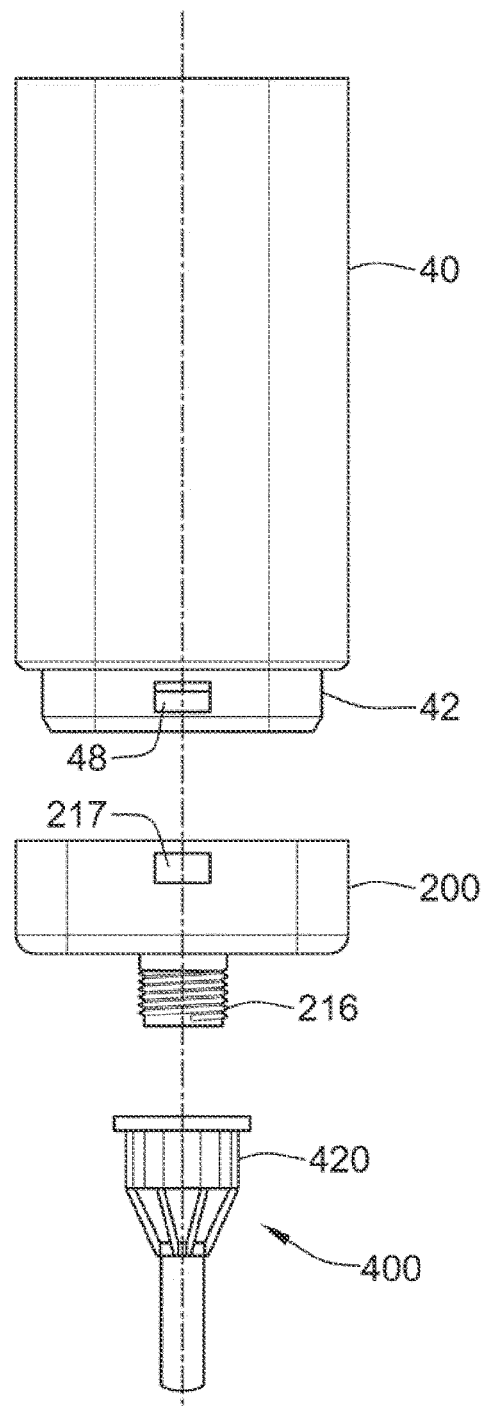
FIG. 4 illustrates a dispense interface and a dose dispenser that may be removably mounted on a distal end of the delivery device illustrated in FIG. 1.

As mentioned above when discussing FIG. 1, a dispense interface 200 can be coupled to the distal end of the cartridge holder 40. FIG. 4 illustrates a flat view of the dispense interface 200 unconnected to the distal end of the cartridge holder 40. A dose dispenser or needle assembly that may be used with the interface 200 is also illustrated and is provided in a protective outer cap 420.

Figure 5:
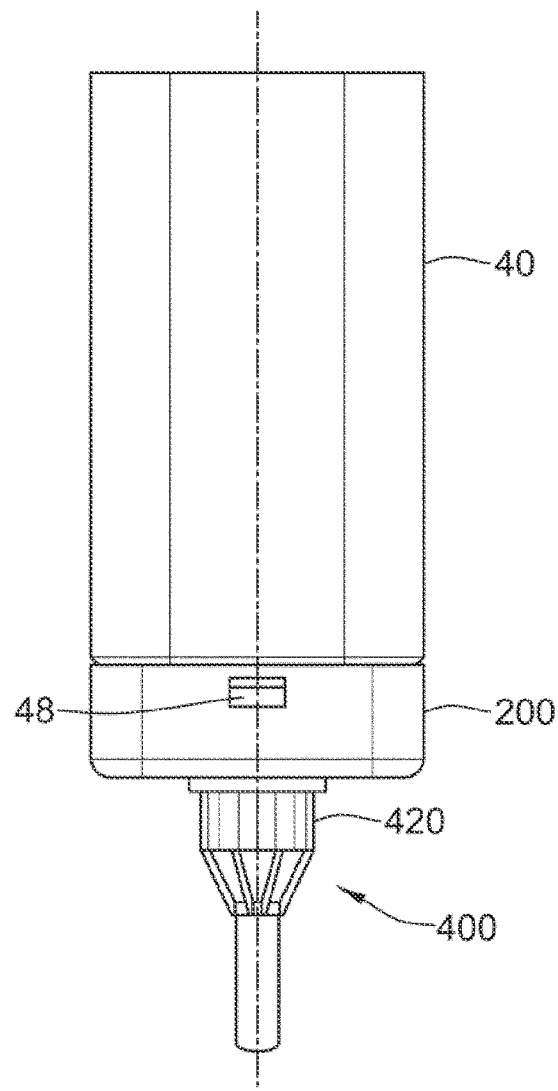
FIG. 5 illustrates the dispense interface and the dose dispenser illustrated in FIG. 4 mounted on a distal end of the delivery device illustrated in FIG. 1.

In FIG. 5, the dispense interface 200 illustrated in FIG. 4 is shown coupled to the cartridge holder 40. The axial attachment means 48 between the dispense interface 200 and the cartridge holder 40 can be any known axial attachment means to those skilled in the art, including snap locks, snap fits, snap rings, keyed slots, and combinations of such connections. The connection or attachment between the dispense interface and the cartridge holder may also contain additional features (not shown), such as connectors, stops, splines, ribs, grooves, pips, clips and the like design features, that ensure that specific hubs are attachable only to matching drug delivery devices. Such additional features would prevent the insertion of a non-appropriate secondary cartridge to a non-matching injection device.

Figure 6:
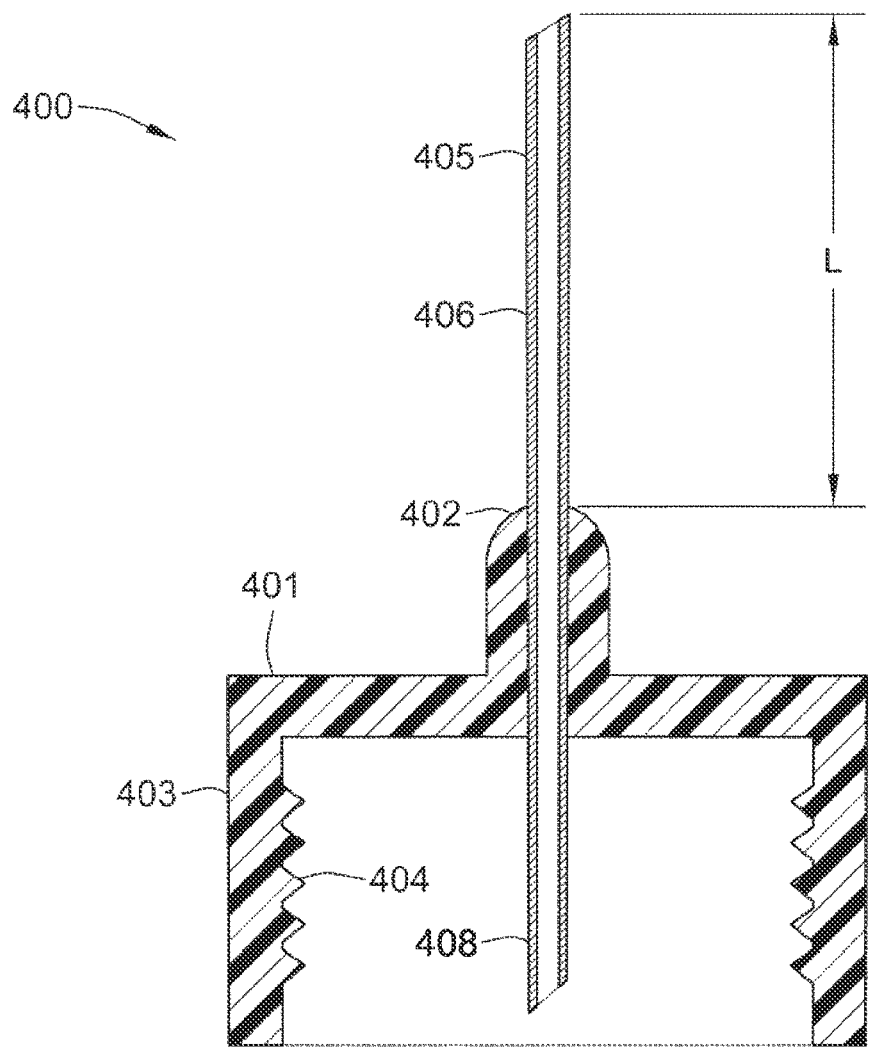
FIG. 6 illustrates one arrangement of a needle assembly that may be mounted on a distal end of the delivery device.
Figure 7:
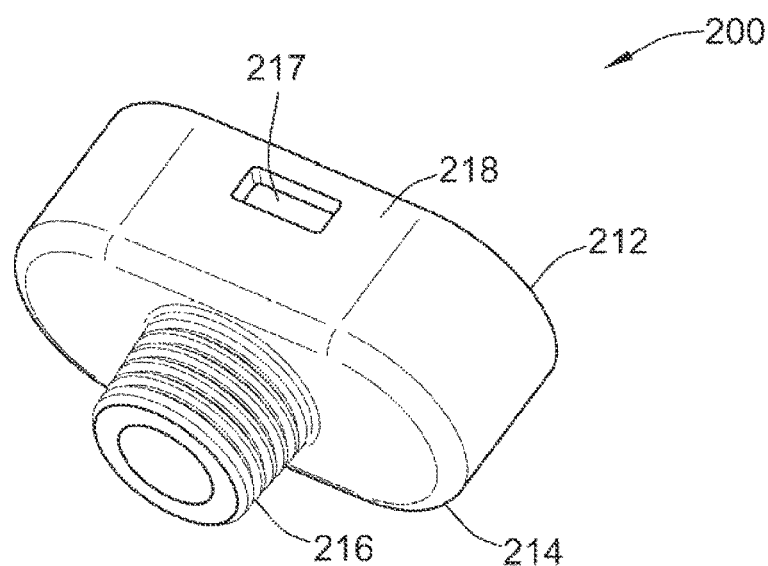
FIG. 7 illustrates a perspective view of the dispense interface illustrated in FIG. 4.

FIG. 5 also illustrates the needle assembly 400 and protective cover 420 coupled to the distal end of the dispense interface 200 that may be screwed onto the needle hub of the interface 200. FIG. 6 illustrates a cross sectional view of the double ended needle assembly 400 mounted on the dispense interface 200 in FIG. 5.

The needle assembly 400 illustrated in FIG. 6 comprises a double ended needle 406 and a hub 401. The double ended needle or cannula 406 is fixedly mounted in a needle hub 401. This needle hub 401 comprises a circular disk shaped element which has along its periphery a circumferential depending sleeve 403. Along an inner wall of this hub member 401, a thread 404 is provided. This thread 404 allows the needle hub 401 to be screwed onto the dispense interface 200 which, in one preferred arrangement, is provided with a corresponding outer thread along a distal hub. At a center portion of the hub element 401 there is provided a protrusion 402. This protrusion 402 projects from the hub in an opposite direction of the sleeve member. A double ended needle 406 is mounted centrally through the protrusion 402 and the needle hub 401. This double ended needle 406 is mounted such that a first or distal piercing end 405 of the double ended needle forms an injecting part for piercing an injection site (e.g., the skin of a user).

Similarly, a second or proximal piercing end 408 of the needle assembly 400 protrudes from an opposite side of the circular disc so that it is concentrically surrounded by the sleeve 403. In one needle assembly arrangement, the second or proximal piercing end 408 may be shorter than the sleeve 403 so that this sleeve to some extent protects the pointed end of the back sleeve. The needle cover cap 420 illustrated in FIGS. 4 and 5 provides a form fit around the outer surface 403 of the hub 401.

Referring now to FIGS. 4 to 11, one preferred arrangement of this interface 200 will now be discussed. In this one preferred arrangement, this interface 200 comprises:

a. a main outer body 210,
   b. an first inner body 220,
   c. a second inner body 230,
   d. a first piercing needle 240,
   e. a second piercing needle 250,
   f. a valve seal 260, and
   g. a septum 270.

The main outer body 210 comprises a main body proximal end 212 and a main body distal end 214. At the proximal end 212 of the outer body 210, a connecting member is configured so as to allow the dispense interface 200 to be attached to the distal end of the cartridge holder 40. Preferably, the connecting member is configured so as to allow the dispense interface 200 to be removably connected the cartridge holder 40. In one preferred interface arrangement, the proximal end of the interface 200 is configured with an upwardly extending wall 218 having at least one recess. For example, as may be seen from FIG. 8, the upwardly extending wall 218 comprises at least a first recess 217 and a second recess 219.

Preferably, the first and the second recesses 217, 219 are positioned within this main outer body wall so as to cooperate with an outwardly protruding member located near the distal end of the cartridge housing 40 of the drug delivery device 10. For example, this outwardly protruding member 48 of the cartridge housing may be seen in FIGS. 4 and 5. A second similar protruding member is provided on the opposite side of the cartridge housing. As such, when the interface 200 is axially slid over the distal end of the cartridge housing 40, the outwardly protruding members will cooperate with the first and second recess 217, 219 to form an interference fit, form fit, or snap lock. Alternatively, and as those of skill in the art will recognize, any other similar connection mechanism that allows for the dispense interface and the cartridge housing 40 to be axially coupled could be used as well.

The main outer body 210 and the distal end of the cartridge holder 40 act to form an axially engaging snap lock or snap fit arrangement that could be axially slid onto the distal end of the cartridge housing. In one alternative arrangement, the dispense interface 200 may be provided with a coding feature so as to prevent inadvertent dispense interface cross use. That is, the inner body of the hub could be geometrically configured so as to prevent an inadvertent cross use of one or more dispense interfaces.

A mounting hub is provided at a distal end of the main outer body 210 of the dispense interface 200. Such a mounting hub can be configured to be releasably connected to a needle assembly. As just one example, this connecting means 216 may comprise an outer thread that engages an inner thread provided along an inner wall surface of a needle hub of a needle assembly, such as the needle assembly 400 illustrated in FIG. 6. Alternative releasable connectors may also be provided such as a snap lock, a snap lock released through threads, a bayonet lock, a form fit, or other similar connection arrangements.

The dispense interface 200 further comprises a first inner body 220. Certain details of this inner body are illustrated in FIG. 8-11. Preferably, this first inner body 220 is coupled to an inner surface 215 of the extending wall 218 of the main outer body 210. More preferably, this first inner body 220 is coupled by way of a rib and groove form fit arrangement to an inner surface of the outer body 210. For example, as can be seen from FIG. 9, the extending wall 218 of the main outer body 210 is provided with a first rib 213a and a second rib 213b. This first rib 213a is also illustrated in FIG. 10. These ribs 213a and 213b are positioned along the inner surface 215 of the wall 218 of the outer body 210 and create a form fit or snap lock engagement with cooperating grooves 224a and 224b of the first inner body 220. In a preferred arrangement, these cooperating grooves 224a and 224b are provided along an outer surface 222 of the first inner body 220.

Figure 8:
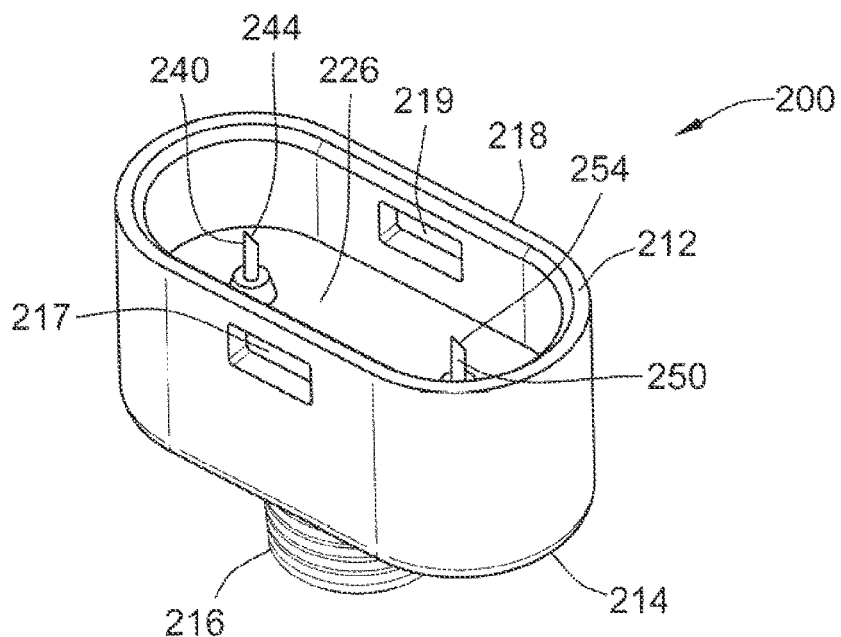
FIG. 8 illustrates another perspective view of the dispense interface illustrated in FIG. 4.
Figure 9:
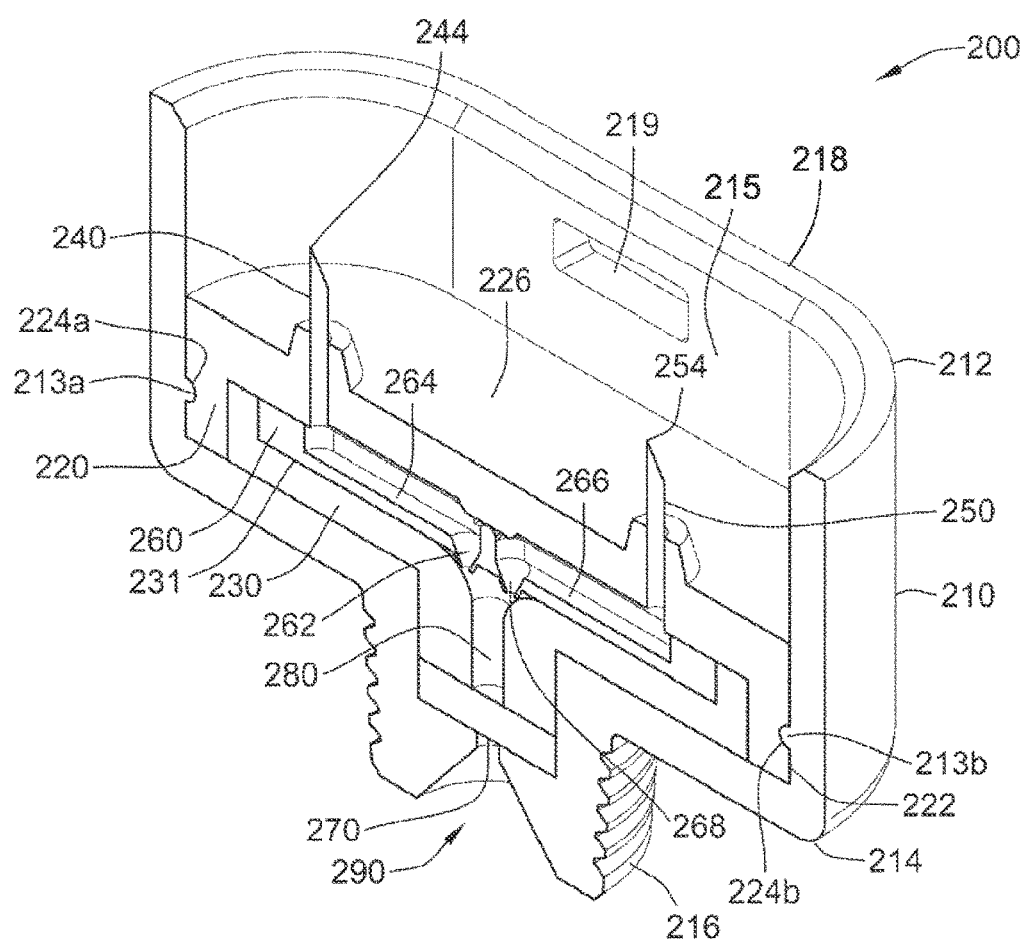
FIG. 9 illustrates a cross-sectional view of the dispense interface illustrated in FIG. 4.
Figure 10:
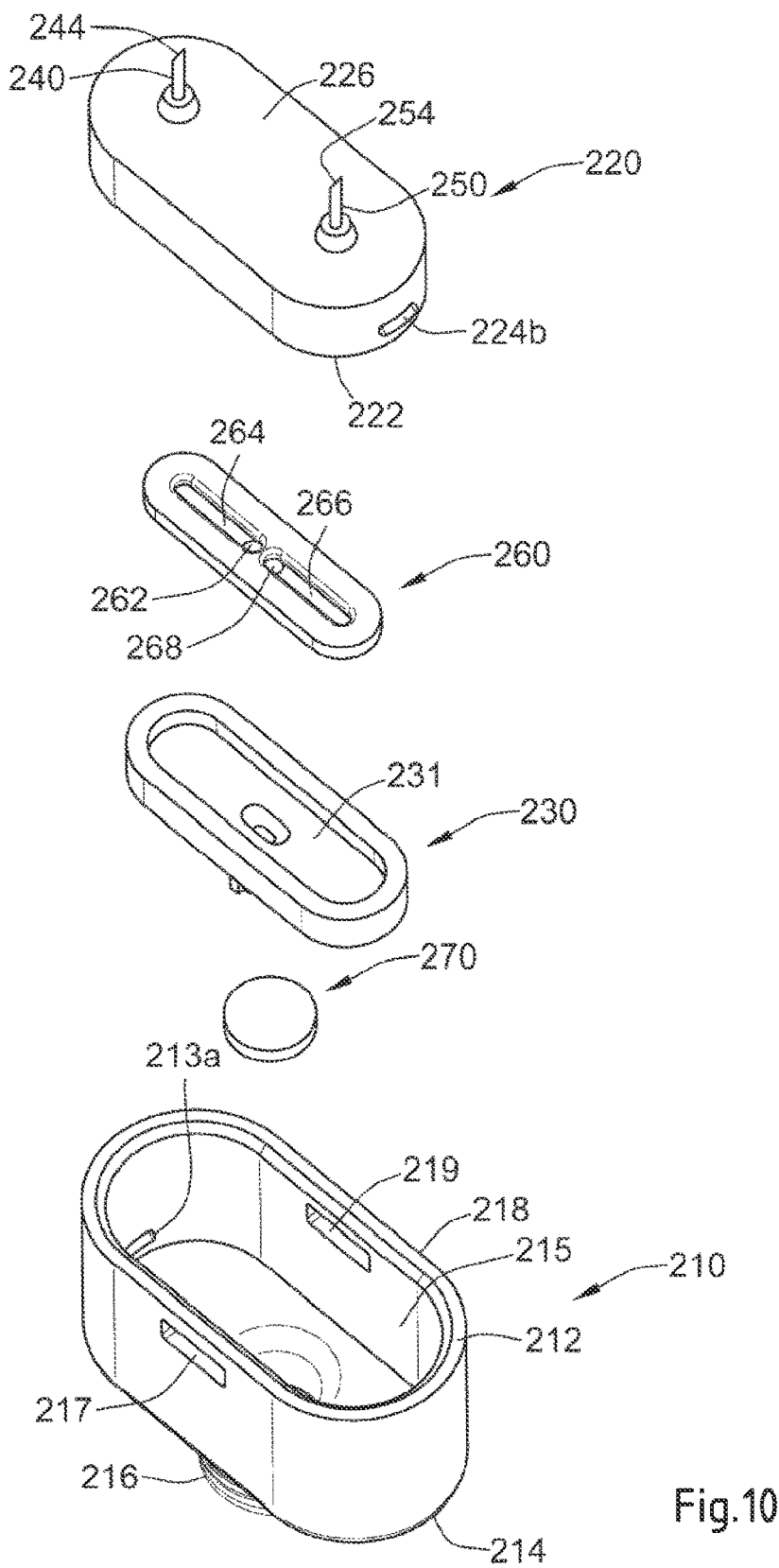
FIG. 10 illustrates an exploded view of the dispense interface illustrated in FIG. 4.

In addition, as can be seen in FIG. 8-10, a proximal surface 226 near the proximal end of the first inner body 220 may be configured with at least a first proximally positioned piercing needle 240 comprising a proximal piercing end portion 244. Similarly, the first inner body 220 is configured with a second proximally positioned piercing needle 250 comprising a proximally piercing end portion 254. Both the first and second needles 240, 250 are rigidly mounted on the proximal surface 226 of the first inner body 220.

Preferably, this dispense interface 200 further comprises a valve arrangement. Such a valve arrangement could be constructed so as to prevent cross contamination of the first and second medicaments contained in the first and second reservoirs, respectively. A preferred valve arrangement may also be configured so as to prevent back flow and cross contamination of the first and second medicaments.

In one preferred system, dispense interface 200 includes a valve arrangement in the form of a valve seal 260. Such a valve seal 260 may be provided within a cavity 231 defined by the second inner body 230, so as to form a holding chamber 280. Preferably, cavity 231 resides along an upper surface of the second inner body 230. This valve seal comprises an upper surface that defines both a first fluid groove 264 and second fluid groove 266. For example, FIG. 9 illustrates the position of the valve seal 260, seated between the first inner body 220 and the second inner body 230. During an injection step, this seal valve 260 helps to prevent the primary medicament in the first pathway from migrating to the secondary medicament in the second pathway, while also preventing the secondary medicament in the second pathway from migrating to the primary medicament in the first pathway. Preferably, this seal valve 260 comprises a first non-return valve 262 and a second non-return valve 268. As such, the first non-return valve 262 prevents fluid transferring along the first fluid pathway 264, for example a groove in the seal valve 260, from returning back into this pathway 264. Similarly, the second non-return valve 268 prevents fluid transferring along the second fluid pathway 266 from returning back into this pathway 266.

Together, the first and second grooves 264, 266 converge towards the non-return valves 262 and 268 respectively, to then provide for an output fluid path or a holding chamber 280. This holding chamber 280 is defined by an inner chamber defined by a distal end of the second inner body both the first and the second non return valves 262, 268 along with a pierceable septum 270. As illustrated, this pierceable septum 270 is positioned between a distal end portion of the second inner body 230 and an inner surface defined by the needle hub of the main outer body 210.

The holding chamber 280 terminates at an outlet port of the interface 200. This outlet port 290 is preferably centrally located in the needle hub of the interface 200 and assists in maintaining the pierceable seal 270 in a stationary position. As such, when a double ended needle assembly is attached to the needle hub of the interface (such as the double ended needle illustrated in FIG. 6), the output fluid path allows both medicaments to be in fluid communication with the attached needle assembly.

The hub interface 200 further comprises a second inner body 230. As can be seen from FIG. 9, this second inner body 230 has an upper surface that defines a recess, and the valve seal 260 is positioned within this recess. Therefore, when the interface 200 is assembled as shown in FIG. 9, the second inner body 230 will be positioned between a distal end of the outer body 210 and the first inner body 220. Together, second inner body 230 and the main outer body hold the septum 270 in place. The distal end of the inner body 230 may also form a cavity or holding chamber that can be configured to be fluid communication with both the first groove 264 and the second groove 266 of the valve seal.

Axially sliding the main outer body 210 over the distal end of the drug delivery device attaches the dispense interface 200 to the multi-use device. In this manner, a fluid communication may be created between the first needle 240 and the second needle 250 with the primary medicament of the first cartridge and the secondary medicament of the second cartridge, respectively.

Figure 11:
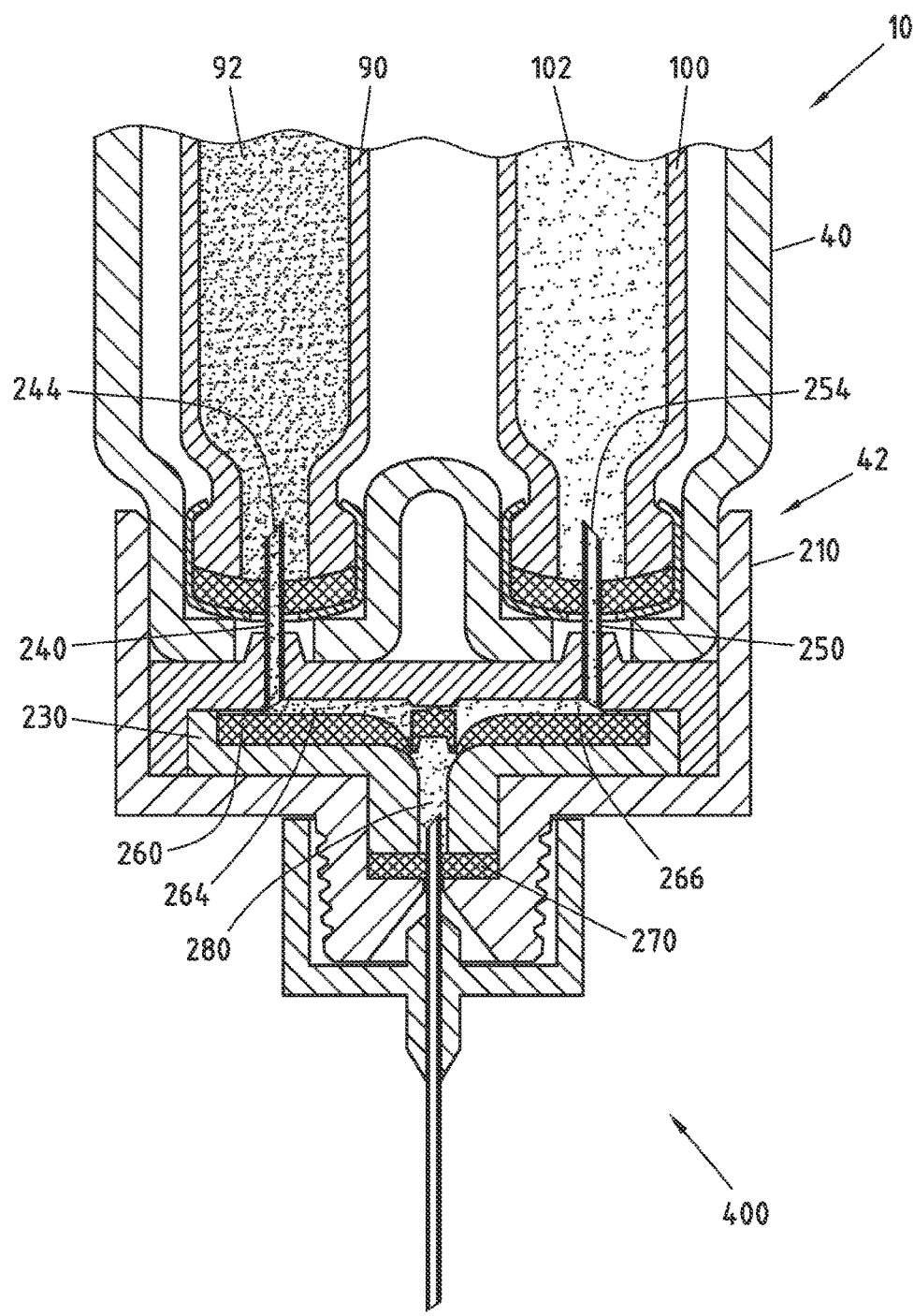
FIG. 11 illustrates a cross-sectional view of the dispense interface and needle assembly mounted onto a drug delivery device, such as the device illustrated in FIG. 1.

FIG. 11 illustrates the dispense interface 200 after it has been mounted onto the distal end 42 of the cartridge holder 40 of the drug delivery device 10 illustrated in FIG. 1. A double ended needle 400 is also mounted to the distal end of this interface. The cartridge holder 40 is illustrated as having a first cartridge containing a first medicament and a second cartridge containing a second medicament.

When the interface 200 is first mounted over the distal end of the cartridge holder 40, the proximal piercing end 244 of the first piercing needle 240 pierces the septum of the first cartridge 90 and thereby resides in fluid communication with the primary medicament 92 of the first cartridge 90. A distal end of the first piercing needle 240 will also be in fluid communication with a first fluid path groove 264 defined by the valve seal 260.

Similarly, the proximal piercing end 254 of the second piercing needle 250 pierces the septum of the second cartridge 100 and thereby resides in fluid communication with the secondary medicament 102 of the second cartridge 100. A distal end of this second piercing needle 250 will also be in fluid communication with a second fluid path groove 266 defined by the valve seal 260.

FIG. 11 illustrates a preferred arrangement of such a dispense interface 200 that is coupled to a distal end 15 of the main body 14 of drug delivery device 10. Preferably, such a dispense interface 200 is removably coupled to the cartridge holder 40 of the drug delivery device 10.

As illustrated in FIG. 11, the dispense interface 200 is coupled to the distal end of a cartridge housing 40. This cartridge holder 40 is illustrated as containing the first cartridge 90 containing the primary medicament 92 and the second cartridge 100 containing the secondary medicament 102. Once coupled to the cartridge housing 40, the dispense interface 200 essentially provides a mechanism for providing a fluid communication path from the first and second cartridges 90, 100 to the common holding chamber 280. This holding chamber 280 is illustrated as being in fluid communication with a dose dispenser. Here, as illustrated, this dose dispenser comprises the double ended needle assembly 400. As illustrated, the proximal end of the double ended needle assembly is in fluid communication with the chamber 280.

In one preferred arrangement, the dispense interface is configured so that it attaches to the main body in only one orientation, that is it is fitted only one way round. As such as illustrated in FIG. 11, once the dispense interface 200 is attached to the cartridge holder 40, the primary needle 240 can only be used for fluid communication with the primary medicament 92 of the first cartridge 90 and the interface 200 would be prevented from being reattached to the holder 40 so that the primary needle 240 could now be used for fluid communication with the secondary medicament 102 of the second cartridge 100. Such a one way around connecting mechanism may help to reduce potential cross contamination between the two medicaments 92 and 102.

Figure 12:
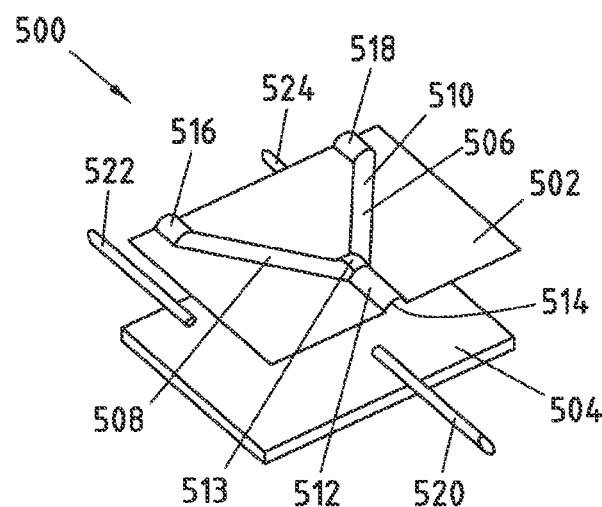
FIG. 12 illustrates a perspective view of a dispense interface according to the invention with two flat parts not joined to each other.

FIG. 12 illustrates a perspective view of a dispense interface 500 according to the invention with two flat parts 502, 504 not joined to each other.

The first flat part 502, in particular a top flat part 502, can be made of a metallic material. For instance, the first flat part 502 is a metallic foil 502, like an aluminium foil 502. Other metallic materials, like copper, brass and the like, can also be used.

The thin metal foil 502 can be easily provided with at least one part of the channel profile 506 of the dispense device 500 in case the metal foil is embossed. Embossing is a process producing raised or sunken designs or relief in sheet metal for in an easy and defined way. This process can be made e.g. by means of matched male and female roller dies, or by passing sheet or a strip of metal, like a metal plate, between rolls of the desired pattern. In the present case, the total channel profile 506 formed by embossing the metal foil 502.

In particular, at least a first deepening 508 or cavity 508 can be formed by embossing. The first deepening 508 forms a first inlet channel 508. At least a second deepening 510 or cavity 510 can be formed by embossing. The second deepening 510 forms a second inlet channel 510. Furthermore, at least a third deepening 512 may be formed by embossing. The third deepening 512 forms an outlet channel 512. At least a further deepening 513 can be formed by embossing. This deepening 513 forms a connecting channel 513. The connecting channel 513 may be configured for a fluid communication between the outlet channel 512 and at least one of the inlet channels 508, 510.

Preferably, the deepenings 508, 510, 512, 513 can be formed in one process step. A cost-efficient production of the dispense interface 500 can be provided.

The second flat part 504, like a base flat part 504, may be also a metallic plate. In the present example, the second flat part 504 can be preferably made of a polymer material. A polymer material comprises generally a lighter weight than a metallic plate and can be produced with reduced costs. Compared with the first metallic plate 502, the second flat part 504 may have a thickness larger than the thickness of the first flat part 502.

As can be seen from FIG. 12, the second flat part 504 is a flat plate 504 without raised or sunken designs, like deepenings. Such a plate 504 can be produced with reduced effort and cost.

The first flat part 502 and the second flat part 504 can be tightly connected to each other. For instance, a bonding technique can be used for connecting both flat parts 502, 504 to each other. A bonding technique can be preferably used in case the two flat parts 502, 504 to be connected are made of different material. In particular, a bonding technique can be used if only one flat part 502 is made of a metallic material while the other flat part 504 is made of a polymer material.

By tightly connecting the two flat parts 502, 504, a channel profile 506 is provided having a substantially semicircular cross section. In particular, the bottom of the channel profile 506 can be provided by the second flat part 504 while the roof of the channel profile 506 is provided by the first flat part 502. It shall be understood that according to other variants of the invention, the cross section of the channel profile 506 may vary along the channel profile. Furthermore, in other variants, the deepenings 508, 510, 512, 513 may have another shape, like an angular shape.

In addition, a first and a second proximal needle 522, 524 and a third needle 520, like an ejection needle 520, are provided. The first and second proximal needle 522, 524 can be tightly integrated in a respective inlet opening 516, 518. For instance, a press-fit connection between a needle 522, 524 and an inlet channel opening 516, 518 is provided. Alternatively, the needle 522, 524 can be integrated by a potting technique.

The third needle 520 can be tightly integrated in a respective outlet opening 514. For instance, a press-fit connection between a needle 520 and an outlet channel opening 514 is provided. Alternatively, the needle 520 can be integrated by a potting technique.

The dispense interface 500 may comprise a valve arrangement. In particular, the channel profile 506 comprises at least one non-return valve. For instance, the connecting channel 513 may comprise such a valve.

Figure 13:
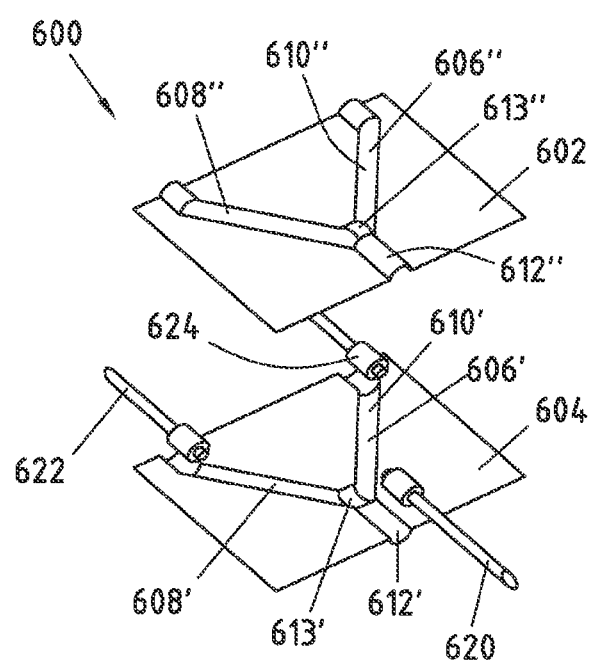
FIG. 13 illustrates a perspective view of a further dispense interface according to the invention with two flat parts not joined to each other.

FIG. 13 illustrates a perspective view of a further dispense interface 600 according to the invention with two flat parts 602, 604 not joined to each other. In this example, both flat parts 602, 604 are made of a metallic material. Preferably, the two flat parts 602, 604 are made of the same material, like aluminium.

As can be seen from FIG. 13, the first flat part 602 comprises a first half channel structure 606". In particular, the first half channel structure 606" can be formed in a similar way, as described in connection of the first flat part 502 of FIG. 12. For instance, a first deepening 608" can be formed by embossing, wherein the first deepening 608" forms at least one part of a first inlet channel 608. A second deepening 610" can be formed by embossing. The second deepening 610" forms at least one part of a second inlet channel 610. Furthermore, a third deepening 612" can be formed by embossing. The third deepening 612" forms at least one part of the outlet channel 612. A further deepening 613" can be formed by embossing. This deepening 613" forms at least one part of a connecting channel 613. The connecting channel 613 may be configured for a fluid communication between the outlet channel 612 and at least one of the inlet channels 608, 610.

In similar way, a second half channel profile 606' can be formed in the second flat part. In particular, at least a first deepening 608' can be formed by embossing. The first deepening 608' forms at least one part of a first inlet channel 608'. In particular, deepening 608' corresponds to deepening 608" and both deepenings 608', 608' form the first inlet channel 608.

A second deepening 610' can be formed by embossing. The second deepening 610' forms at least one part of a second inlet channel 610'. In particular, deepening 610' corresponds to deepening 610" and both deepenings 610', 610' form the second inlet channel 610.

Furthermore, a third deepening 612' may be formed by embossing. The third deepening 612' forms at least one part of the outlet channel 612. In particular, deepening 612' corresponds to deepening 612" and both deepenings 612', 612' form the outlet channel 612.

At least a further deepening 613' can be formed by embossing. This deepening 613' may form at least one part of a connecting channel 613'. In particular, deepening 613' corresponds to deepening 613" and both deepenings 613', 613' form the connecting channel 613.

As previously described, the connecting channel 613 may be configured for a fluid communication between the outlet channel 612 and at least one of the inlet channels 608, 610.

In particular, the first half channel structure 606" corresponds to the second half channel structure 606'. Each deepening 608", 610", 612", 613" of the first flat part 602 may have a corresponding counterpart 608', 610', 612', 613' in the second flat part 604. By tightly connecting the flat parts 602, 604, a full channel structure 606 can be established.

For the sake of clarity, the respective openings of the inlet and outlet channels 608, 610, 612 are not provided with reference signs.

Figure 14:
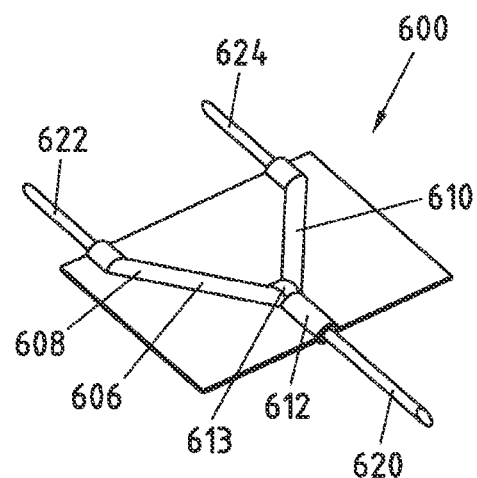
FIG. 14 illustrates a perspective view of the dispense interface of FIG. 13 with two flat parts joined to each other.

FIG. 14 illustrates a perspective view of the dispense interface 600 of FIG. 13 with the two flat parts 602, 604 joined to each other. The two flat parts 602, 604 are tightly connected to each other. For instance, the first and second flat parts 602, 604 are tightly connected to each other by ultrasonic welding techniques, heat sealing techniques, adhesive bonding techniques and/or spot welding techniques. As can be further seen, the first and second proximal needle 622, 624 are tightly integrated in the dispense interface 600. Furthermore, the third needle 620 is tightly integrated in the dispense device 600. A compact dispense interface 600 is provided.

The dispense interface 600 may comprise a valve arrangement. In particular, the channel profile 606 comprises at least one non-return valve. For instance, the connecting channel 613 may comprise such a valve.

Figure 15:
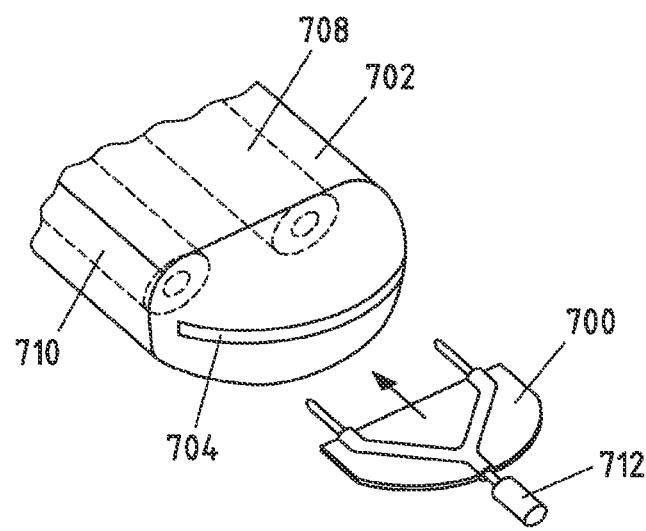
FIG. 15 illustrates a perspective view of a system according to the invention.

FIG. 15 illustrates a perspective view of a system according to the invention. An ejection device 702 with at least a first reservoir 708 and a second reservoir 710 is shown. The ejection device 702 comprises an intake 704 having guiding means for an easy attachment of the dispense interface 700. The user can manually attach the dispense interface 700 to the intake 704 of the ejection device 702.

After removing the cap 712, the user can operate the ejection device 702. At least one fluid of at least one reservoir can be ejected through the dispense interface 700. Then the dispense interface 700 can be removed from the ejection device 702. For instance, the dispense interface 700 can be discarded.

FIGS. 16a to 16e illustrates valve arrangements 3000a to 3000e, wherein at least one of these valve arrangements 3000a to 3000e can be integrated into a previously described dispense interface 500, 600.

Figure 16A:
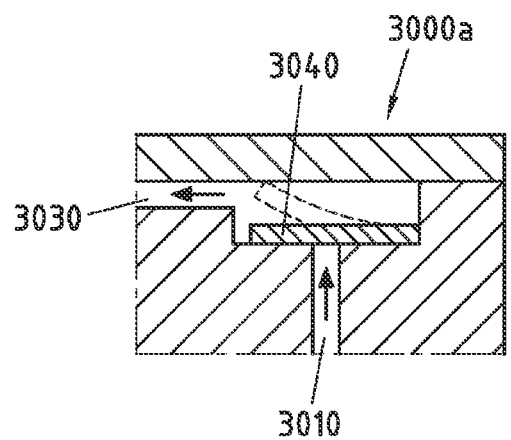
FIG. 16 illustrates perspective views of valve elements, which can be used in a dispense interface according to the invention.

FIG. 16a illustrates a diaphragm/flap valve arrangement 3000a. The diaphragm/flap valve arrangement 3000a has an inlet 3010 and an outlet 3030. The inlet 3010 may for instance reside in fluid communication with one of the piercing needles 240, 250 of dispense interface 200 or with one of the piercing needles 522, 524 of dispense interface 500 or with one of the piercing needles 622, 624 of dispense interface 600, and the outlet 3030 may for instance reside in fluid communication with holding chamber 280 of dispense interface 200 or with the ejection needle 520 of dispense interface 500 or with the ejection needle 620 of dispense interface 600.

The diaphragm/flap valve arrangement 3000a has flexible diaphragm/flap 3040. When the fluidic pressure in the inlet 3010 is increased (e.g. during a dose priming or a dose injecting step), the diaphragm/flap 3040 will change from an un-stressed state to a stressed state. In the stressed state, the fluidic pressure bends the diaphragm/flap 3040 as indicated by the arrow in FIG. 16a so that the diaphragm/flap valve arrangement 3000a opens. In this stressed condition, the diaphragm/flap valve arrangement 3000a will allow fluid to flow from the inlet 3010 to the outlet 3030. When the fluidic pressure in the inlet is removed, the diaphragm/flap 3040 will return to its initial position and seal the inlet 3010, preventing backflow.

Figure 16B:
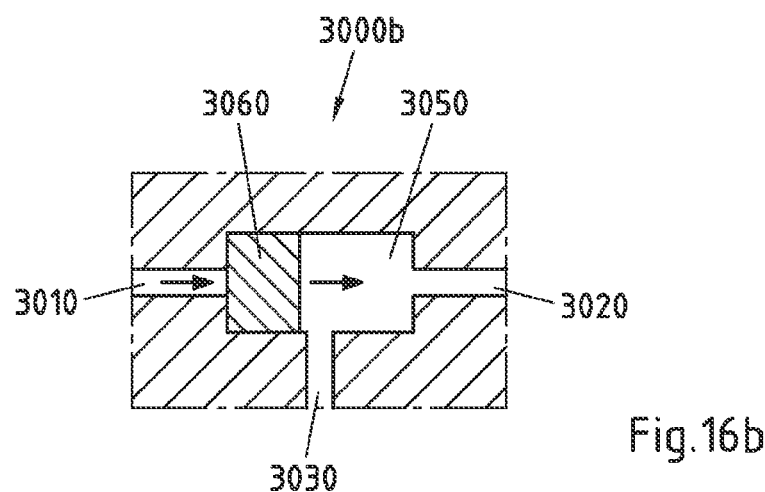

FIG. 16b illustrates a shuttling valve arrangement 3000b. The shuttling valve arrangement 3000b has a tube 3050. The tube 3050 has two inlets 3010, 3020 and an outlet 3030. In the tube 3050 a movable element 3060 (e.g. a piston or a ball) is arranged.

The diameter of the movable element 3060 corresponds to the diameter of the tube 3050 such that the movable element 3060 is movable between a first and a second (longitudinal) position in the tube 3050. In the first position (illustrated in FIG. 16b), the movable element 3060 seals the inlet 3010 and allows fluid flow from the inlet 3020 to the outlet 3030. In the second position (not illustrated), the movable element 3060 seals the inlet 3020 and allows fluid flow from the inlet 3010 to the outlet 3030. When the fluidic pressure in the inlet 3010 is for instance increased (e.g. during a dose priming or a dose injecting step), the movable element 3060 will be pushed towards the second position as indicated by the arrow in FIG. 16b.

Figure 16C:
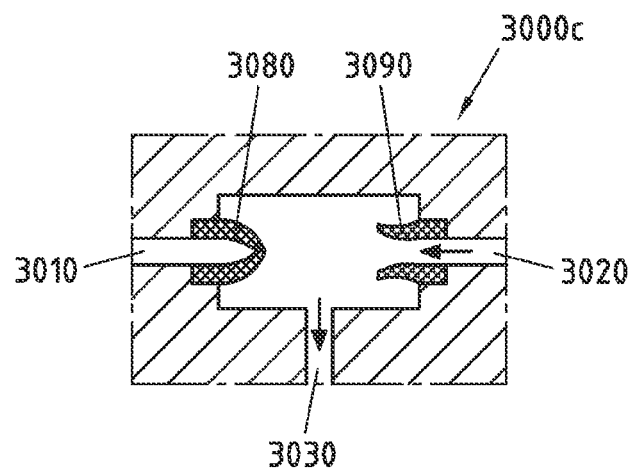

FIG. 16c illustrates a moulded duckbill valve arrangement 3000c. The moulded duckbill valve arrangement 3000c has a first and a second duckbill valve 3080, 3090. When the fluidic pressure in the inlet 3020 is increased (e.g. during a dose priming or a dose injecting step), the second duckbill valve 3090 will change from an un-stressed state to a stressed state. In the stressed state, the fluidic pressure inverts the naturally flattened shape of the duckbill valve as indicated in FIG. 16c so that the duckbill valve opens. In this stressed condition, the second duckbill valve 3090 will allow fluid to flow from the inlet 3020 to the outlet 3030. When the fluidic pressure in the inlet 3020 is removed, the second duckbill valve 3090 will return to its flattened shape and seal the inlet 3020, preventing backflow. The first duckbill valve 3080 operates in a similar manner as the second duckbill valve 3090 when the fluidic pressure is increased in the inlet 3010.

Figure 16D:
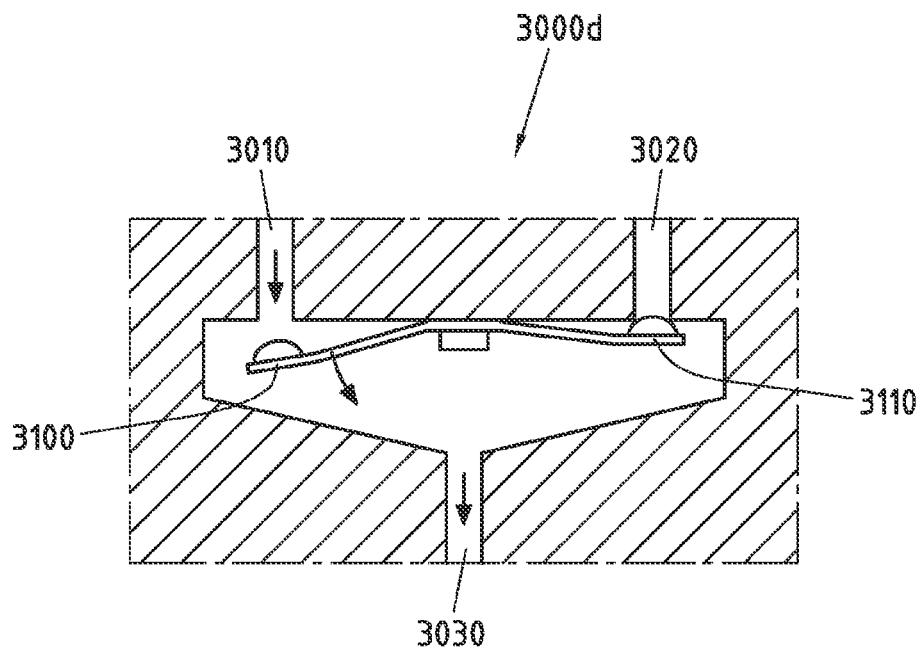

FIG. 16d illustrates a flat spring valve arrangement 3000d. The flat spring valve arrangement 3000d has a first and a second flat spring 3100, 3110. The first and the second flat spring 3100, 3110 may for instance be integrally formed.

When the fluidic pressure in the inlet 3010 is increased (e.g. during a dose priming or a dose injecting step), the first flat spring 3100 will change from an un-stressed state to a stressed state. In the stressed state, the fluidic pressure bends the first flat spring 3100 as indicated by the arrow in FIG. 16d so that the flat spring valve arrangement 3000d opens. In this stressed condition, the flat spring valve arrangement 3000d will allow fluid to flow from the inlet 3010 to the outlet 3030. When the fluidic pressure in the inlet is removed, the first flat spring 3100 will return to its initial position and seal the inlet 3010, preventing backflow. The second flat spring 3110 operates in a similar manner as the first flat spring 3100 when the fluidic pressure is increased in the inlet 3020.

Figure 16E:
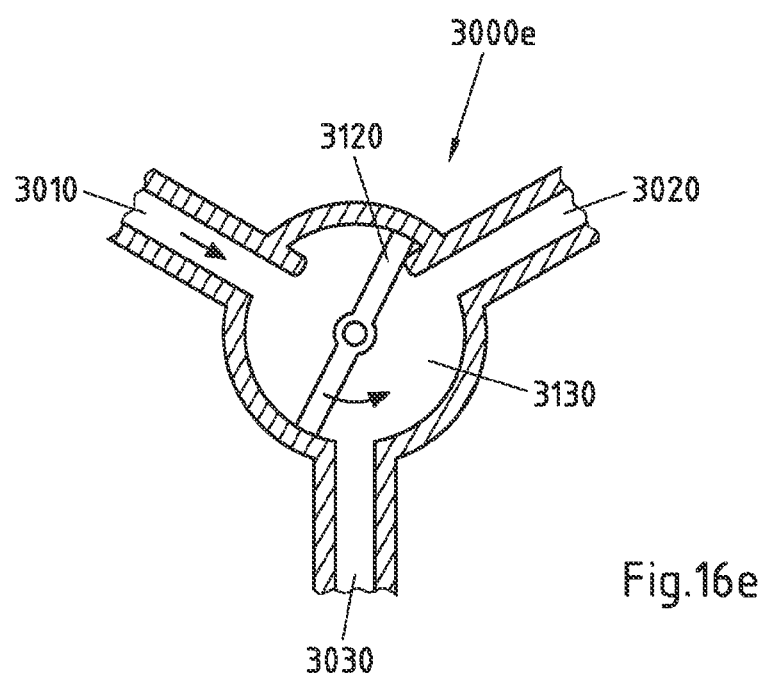

FIG. 16e illustrates a rotating flap valve arrangement 3000e. The rotating flap valve arrangement 3000e has a flap 3120 which is rotatably mounted in a valve chamber 3130. The valve chamber has two inlets 3010, 3020 and an outlet 3030.

The flap 3120 is rotatable between a first and a second position. In the first position (illustrated in FIG. 16e), the flap 3120 seals the inlet 3010 and allows fluid flow from the inlet 3020 to the outlet 3030. In the second position (not illustrated), the flap 3120 seals the inlet 3020 and allows fluid flow from the inlet 3010 to the outlet 3030.

When the fluidic pressure in the inlet 3010 is for instance increased (e.g. during a dose priming or a dose injecting step), the flap 3120 will be pushed towards the second position as indicated by the arrow in FIG. 16e.

Figure 17:
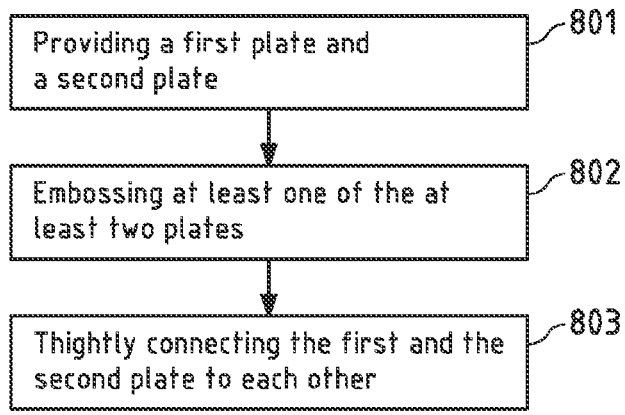
FIG. 17 illustrates a flowchart of a method according to the invention for manufacturing a dispense interface.

FIG. 17 illustrates a flowchart of a method according to the invention for manufacturing a dispense interface, like one of the previously described dispense interfaces. In a first step 801, at least a first and a second flat part can be provided. For instance, a flat metallic sheet, like a metallic foil, and a flat polymer sheet can be provided. Alternatively, two metallic sheets, like two metallic foils can be provided.

At least one of the two flat parts can be embossed in the next step 802. In particular, the at least one metallic plate is cold-embossed. Thereby, at least a part of the channel structure can be introduced into the first metallic plate in form of at least one deepening.

Optionally, in particular if the second flat part is also a metallic plate, at least a part of the channel structure can be introduced into the second metallic plate in form of at least one deepening. In this case, the at least one deepening of the first flat part can preferably correspond to the deepening of the second flat part. That means that when both flat parts are tightly connected, a channel is formed by the deepening of the first flat part and by the corresponding deepening of the second flat part.

Then the at least two flat parts can be tightly connected to each other (step 803). For instance, ultrasonic welding techniques, heat sealing techniques, adhesive bonding techniques and/or spot welding techniques can be used. As previously explained, if both flat parts comprise deepenings, the two flat parts can be connected to each other in such a way that a channel profile is formed. In particular, the corresponding deepenings are arranged directly one above the other.

Before connecting the at least two flat parts to each other, at least one needle, preferably a first proximal needle, a second proximal needle and an ejection needle can be provided. In particular, the respective needles can be inserted into the respective inlet openings and outlet opening. Then the flat parts can be tightly connected to each other. At the same time, in particular in the same process step, the needles are tightly integrated.

Alternatively, after connecting the at least two flat parts, the respective needles can be inserted in the respective openings. A tight connection can be achieved by a press-fit connection, for instance.

Figure 18:
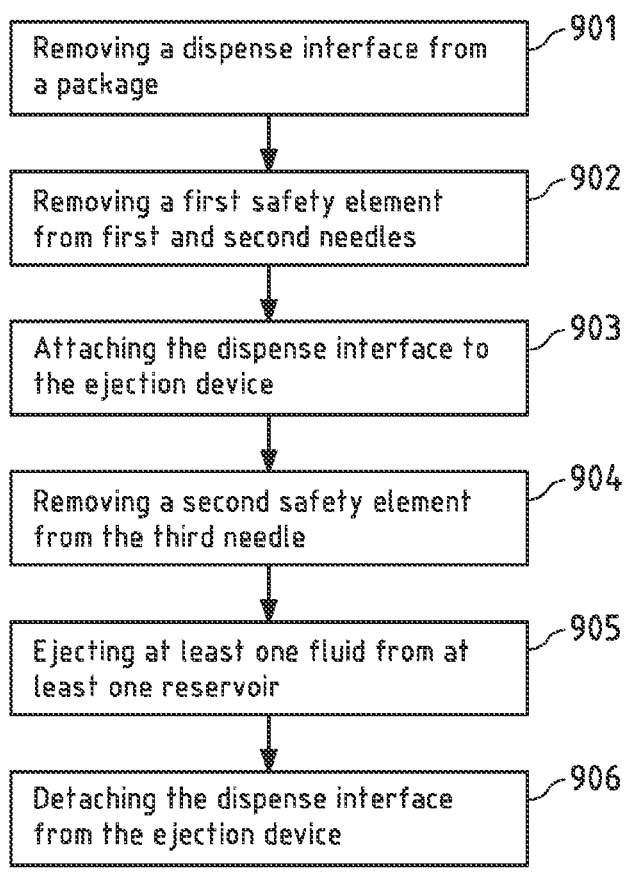
FIG. 18 illustrates a flowchart of a method according to the invention for using a dispense interface.

FIG. 18 illustrates a flowchart of a method according to the invention for using a dispense interface. In particular, the use of a previously described dispense interface is illustrated.

In a first step 901, a package of the dispense interface can be opened by a user and the dispense interface can be taken from the package.

Then, in step 902, if the dispense interface is provided with a first safety element, like a needle cover for the proximal needles, the first safety element can be removed from the first proximal needle and the second proximal needle.

After removing the first safety element, the first and second proximal needles are exposed. Then in step 903, the dispense interface is attached to an ejection device. In particular, the dispense interface is tightly attached to the ejection device. Thereby, the first proximal needle can puncture a first reservoir and the second proximal needle can puncture a second reservoir of the ejection device.

If the dispense interface comprises a second safety element, like a needle cover for the distal or injection needle, in step 904, the second safety element is removed. The third needle, like an injection needle, is exposed.

In the next step 905, at least one fluid of at least one reservoir can be ejected, as described hereinbefore. For instance, a drug or medicament can be ejected through the dispense interface.

Afterwards, the used dispense interface is detached from the ejection device (step 906). For instance, the used dispense interface can be pulled out by a user. The used dispense interface can be discarded.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyhepta-decanoyl) human insulin.

Exendin-4 for example means Exendin-4(1-39), a peptide of the sequence H His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser- Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;

or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4 (1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4 (1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4 (1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2) 25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2) 25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystallizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline earth metal, e.g. Na+, or K+, or Ca2+, or an ammonium ion N+(R1)(R2)(R3)(R4), wherein R1 to R4 independently of each other mean: hydrogen, an optionally substituted C1 C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The invention claimed is:

1. A dispense interface comprising:
a first part having a generally flat lower surface defining a plane; and
a second part having a generally flat upper surface defining a plane,
wherein the first part comprises at least one deepening in the lower surface that extends out of the plane and is configured as a roof of a channel profile,
wherein the second part is tightly connected to the first part through direct contact of the generally flat lower surface and the generally flat upper surface such that a portion of the second part forms a bottom of the channel profile so that fluid can flow within the channel profile,
wherein the at least one deepening is formed by embossing,
wherein the channel profile comprises at least two inlet channels and at least one outlet channel, and
wherein each of the at least two inlet channels is configured for fluid communication with a respective reservoir of at least two reservoirs, and wherein each of the at least two inlet channels and the at least one outlet channel is formed with a needle that is tightly integrated into the at least two inlet channels and the at least one outlet channel by press-fitting and/or potting.

2. The dispense interface according to claim 1,
wherein the first part comprises a first deepening configured for forming at least one part of the first inlet channel,
wherein the first part comprises a second deepening configured for forming at least one part of the second inlet channel, and
wherein the first part comprises a third deepening configured for forming at least one part of the outlet channel.

3. The dispense interface according to claim 1, wherein the first part is a metallic plate.

4. The dispense interface according to claim 3, wherein the metallic plate is a metallic foil comprising a thickness of at most 0.2 mm.

5. The dispense interface according to claim 1, wherein the second part is made of a polymer material.

6. The dispense interface according to claim 1, wherein at least one part of the channel profile is formed by embossing at least the first part and the second part.

7. The dispense interface according to claim 6, wherein at least one deepening configured for forming at least one part of a first half channel profile is formed in the first part, and
wherein at least one deepening for forming at least one part of a second half channel profile corresponding to the first half channel profile is formed in the second part.

8. The dispense interface according to claim 1, wherein the second part is tightly connected to the first part by ultrasonic welding techniques, heat sealing techniques, adhesive bonding techniques and/or spot welding techniques.

9. The dispense interface according to claim 1, wherein each of the at least two inlet channels comprises an inlet opening, and
wherein the at least one outlet channel comprises an outlet opening.

10. The dispense interface according to claim 1, wherein the channel profile comprises at least one non-return valve.

11. A method for manufacturing a dispense interface comprising:
providing at least a first part having a generally flat lower surface defining a plane and a second part having a generally flat upper surface defining a plane,
forming at least one deepening into at least one of the lower surface and the upper surface by embossing,
tightly connecting the first part to the second part through direct contact of the generally flat lower surface to the generally flat upper surface, thereby forming a first inlet channel, a second inlet channel, and an outlet channel, wherein each of the first and second inlet channels comprises an inlet opening, and wherein the outlet channel comprises an outlet opening; and
inserting a needle into each of the first inlet channel, the second inlet channel, and the outlet channel such that the needles are tightly integrated into each of the inlet and outlet openings of each of the respective inlet and outlet channels by press-fitting and/or potting.

12. A system comprising:
a dispense interface according to claim 1, and an ejection device, wherein the dispense interface is attached to the ejection device.

13. The system according to claim 12, wherein the ejection device is a medical device for delivering at least two drug agents from at least two separate reservoirs.

14. A method for using a system comprising an injection device and a dispense interface, where the dispense interface comprises:
a first part having a generally flat lower surface defining a plane; and
a second part having a generally flat upper surface defining a plane,
wherein the first part comprises at least one deepening in the lower surface that extends out of the plane and is configured as a roof of a channel profile,
wherein the second part is tightly connected to the first part through direct contact of the generally flat lower surface and the generally flat upper surface such that a portion of the second part forms a bottom of the channel profile so that fluid can flow within the channel profile,
wherein the at least one deepening is formed by embossing,
wherein the channel profile comprises at least two inlet channels and at least one outlet channel, wherein each of the two inlet channels comprises an inlet opening, and wherein the outlet channel comprises and outlet opening, and
wherein each of the at least two inlet channels is configured for fluid communication with a respective reservoir of at least two reservoirs, and wherein each of the at least two inlet channels and the at least one outlet channel is formed with a needle that is tightly integrated into the at least two inlet channels and the at least one outlet channel by press-fitting and/or potting;
wherein the method comprises:
attaching the dispense interface to an ejection device having at least two reservoirs such that a fluid tight connection is established between said at least two reservoirs and the dispense interface;
ejecting a fluid from at least one of the reservoirs out of the dispense interface; and
detaching the dispense interface from the ejection device.

15. The dispense interface according to claim 1,
wherein the generally flat upper surface of the second part does not have a raised or sunken design or a deepening.

\* \* \* \* \*